United States Patent
Weithmann et al.

(10) Patent No.: US 6,933,298 B2
(45) Date of Patent: Aug. 23, 2005

(54) PYRIDINE-2,4-DICARBOXYLIC ACID DIAMIDES AND PYRIMIDINE-4,6-DICARBOXYLIC ACID DIAMIDES AND THE USE THEREOF FOR SELECTIVELY INHIBITING COLLAGENASES

(75) Inventors: Klaus-Ulrich Weithmann, Hofheim (DE); Jörg Habermann, Bad Soden (DE); Herbert Kogler, Glashütten (DE); Reinhard Kirsch, Braunschweig (DE); Volkmar Wehner, Sandberg (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 9 days.

(21) Appl. No.: 10/065,994

(22) Filed: Dec. 9, 2002

(65) Prior Publication Data

US 2003/0229103 A1 Dec. 11, 2003

Related U.S. Application Data

(60) Provisional application No. 60/358,887, filed on Feb. 22, 2002.

(30) Foreign Application Priority Data

Dec. 8, 2001 (DE) .......................... 101 60 357

(51) Int. Cl.[7] ................... C07D 239/26; C07D 403/12; C07D 403/14; A61K 31/506; A61P 35/00
(52) U.S. Cl. ................... 514/256; 544/333; 544/335; 546/323
(58) Field of Search ................ 544/333, 335; 514/256

(56) References Cited

FOREIGN PATENT DOCUMENTS

| EP | 0418797 | 8/1994 |
|---|---|---|
| EP | 0463592 | 8/1994 |
| EP | 0606046 B1 | 10/1997 |
| WO | WO94/28889 | 12/1994 |
| WO | WO02/064568 A1 | 8/2002 |
| WO | WO02/064571 A1 | 8/2002 |

OTHER PUBLICATIONS

{Leeman et al. Critical Review in Biochemistry and Molecular Biology, 37(3):149–166(2002)}.*
Massova, I. et al., Matrix Metalloproteinases: Structures, Evolution, and Diversification, The FASEB Journal, 1998, (12), pp. 1075–1095.
Veb Deutscher Verlag der Wissenschaften, Methodenregister, Organikum, Organisch Chemisches Grundpraktikum, 15. Aufl., 1976, p. 822.
Weithmann, K.U. et al., Effects of Tiaprofenic Acid on Urinary Pyridinium Crosslinks in Adjuvant Arthritic Rats: Comparison with Doxycycline, Inflammation Research, 1997, (46), pp. 246–252.

* cited by examiner

*Primary Examiner*—Mark L. Berch
*Assistant Examiner*—Kahsay Habte
(74) *Attorney, Agent, or Firm*—Joseph D. Rossi

(57) ABSTRACT

Pyridine-2,4-dicarboxylic acid diamides and pyrimidine-4, 6-dicarboxylic acid diamides of formula I. These compounds are found to possess the property of selectively inhibiting collagenase (MMP). They may therefore be useful in prophylaxis and therapy of diseases whose course involves an increased activity of matrix metalloproteinase 13.

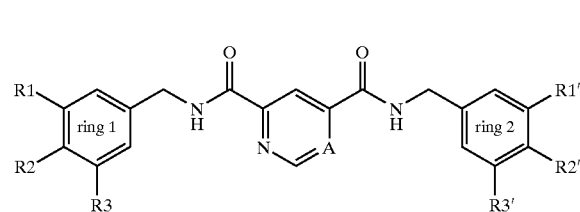

17 Claims, No Drawings

PYRIDINE-2,4-DICARBOXYLIC ACID DIAMIDES AND PYRIMIDINE-4,6-DICARBOXYLIC ACID DIAMIDES AND THE USE THEREOF FOR SELECTIVELY INHIBITING COLLAGENASES

CROSS REFERENCE TO RELATED APPLICATIONS

This application claims the benefit of U.S. Provisional Application No. 60/358,887, filed on Feb. 22, 2002, and German Application No. 10160357.6, filed on Dec. 12, 2001.

BACKGROUND OF INVENTION

This invention relates to the use of pyridine-2,4-dicarboxylic acid diamides and pyrimidine-4,6-dicarboxylic diamides for selectively inhibiting collagenase (MMP 13). The pyridine-2,4-dicarboxylic acid diamides and pyrimidine-4,6-dicarboxylic acid diamides can therefore be employed for treating degenerative diseases of the joints.

It is known that pyrimidine-4,6-dicarboxylic acid diamides and 2,4-substituted pyridine-N-oxides inhibit the enzymes proline hydroxylase and lysine hydroxylase and thereby bring about an inhibition of collagen synthesis by influencing the collagen-specific hydroxylation reaction (EP 0418797; EP 0463592). This inhibition of collagen synthesis results in the formation of a nonfunctional, underhydroxylated collagen molecule which can only be released by the cells into the extracellular space in small quantity. In addition, the underhydroxylated collagen cannot be incorporated into the collagen matrix and is very easily broken down proteolytically. As a consequence of these effects, the overall quantity of extracellularly deposited collagen decreases.

In diseases such as osteoarthritis and rheumatism, the joint is destroyed, due, in particular, to the proteolytic degradation of collagen by collagenases. Collagenases belong to the metalloproteinase (MP) or matrix metalloproteinase (MMP) superfamily. MMPs cleave collagen, laminin, proteoglycans, elastin or gelatin under physiological conditions and therefore play an important role in bone and connective tissue. A large number of different inhibitors of the MMPs or the collagenases are known (EP 0 606 046; WO94/28889). The known inhibitors of the MMPs frequently suffer from the disadvantage that they lack the specificity of inhibiting only one class of the MMPs. As a result, most MMP inhibitors inhibit several MMPs at the same time because the catalytic domains of the MMPs exhibit similar structures. As a consequence, the inhibitors act, in an undesirable manner, on many enzymes, including those, which have a vital function (Massova I., et al., The FASEB Journal (1998) 12, 1075–1095).

In an endeavor to find active compounds for treating connective tissue diseases, it has now been found that the compounds, which are employed in accordance with the invention are powerful inhibitors of matrix metalloproteinase 13 whereas they are essentially inactive in the case of MMPs 3 and 8.

SUMMARY OF INVENTION

The invention therefore relates to the composition and the use of compounds of formula I

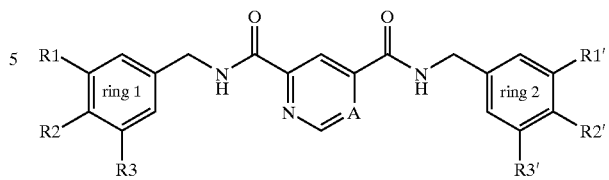

wherein

A is a carbon atom or nitrogen atom;

R1 and R3 are independently selected from the group consisting of hydrogen, halogen, —(C1–C4)-alkyl, in which alkyl is unsubstituted or substituted once, twice or three times by halogen, —O—(C1–C4)-alkyl, In which alkyl is unsubstituted or substituted once, twice or three times by halogen,

—C(O)—O—R4,

—CN,

—N(R5)-(R6),

—OH,

—S—(C1–C4)-alkyl,

—S(O)—(C1–C4)-alkyl and

—S(O)2—R7, and

R2 is selected from the group consisting of hydrogen, halogen, (C1–C4)-alkyl,

—O—(C1–C4)-alkyl,

—C(O)—O—R4,

—CN,

—N(R5)-(R6),

—OH,

—S—(C1–C4)-alkyl,

—S(O)—(C1–C4)-alkyl and

—S(O)2—R7; or R1 and R2, taken together with the two carbon atoms of ring1 to which R1 and R2 are attached, form a 5- or 6-membered ring which is aromatic or saturated and contains zero, one or two heteroatoms which are independently selected from the group consisting of oxygen, nitrogen and sulfur while R3 is as defined above; or R2 and R3, taken together with the two carbon atoms of ring1 to which R2 and R3 are attached, form a 5- or 6-membered ring which is aromatic or saturated and contains zero, one or two heteroatoms which are independently selected from the group consisting of oxygen, nitrogen and sulfur while R1 is not part of a ring and is as defined above;

R1' and R3' are independently selected from the group consisting of hydrogen, halogen, —(C1–C4)-alkyl, in which alkyl is unsubstituted or substituted once, twice or three times by halogen, —O—(C1–C4)-alkyl, in which alkyl is unsubstituted or substituted once, twice or three times by halogen, —C(O)—O—R4,
—CN,
—N(R5)-(R6),
—OH,
—S—(C1–C4)-alkyl,
—S(O)—(C1–C4)-alkyl and
5(O)2—R7, and R2' is selected from the group consisting of
hydrogen,
halogen,
(C1–C4)-alkyl,
—O—(C1–C4)-alkyl,
—C(O)—O—R4,
—CN,
—N(R5)-(R6),
—OH,
—S—(C1–C4)-alkyl,
—S(O)—(C1–C4)-alkyl and
—S(O)2—R7; or R1' and R2', taken together with the two carbon atoms of ring2 to which R1' and R2'are attached, form a 5- or 6-membered ring which is aromatic or saturated and contains zero, one or two heteroatoms which are independently selected from the group consisting of oxygen, nitrogen and sulfur while R3' is as defined above; or R2' and R3', taken together with the two carbon atoms of ring2 to which R2' and R3' are attached, form a 5- or 6-membered ring which is aromatic or saturated and contains zero, one or two heteroatoms which are independently selected from the group consisting of oxygen, nitrogen and sulfur while R1' is not a number of a ring and is as defined above;

R4 is hydrogen or (C1–C4)-alkyl;
R5 and R6 are independently selected from the group consisting of hydrogen, —(C1–C4)-alkyl, —C(O)—(C1–C4)-alkyl and —SO2—(C1–C4)-alkyl; and
R7 is selected from the group consisting of-(C1–C4)-alkyl, OH and NH2;

provided that at least one of the radicals R1, R2, R3, R1', R2', R3' is not selected from the group consisting of hydrogen, halogen, nitro, —(C1–C4)-alkyl and —O—(C1–C4)-alkyl.

The invention furthermore relates to the composition and the use of compounds of formula I as defined above except that there is no 5- or 6-membered ring formed between R1 and R2, or between R2 and R3, or between R1'and R2', or between R2'and R3' and that R1, R3, R1', and R3' are not selected from the group consisting of halogen, unsubstituted —(C1–C4)-alkyl and unsubstituted —O—(C1–C4)-alkyl.

The invention furthermore relates to the composition and the use of compounds of formula 1, wherein R1, R3, R1', and R3'are independently selected from the group consisting of hydrogen, chlorine, fluorine, trifluoromethyl, methoxy, methyl, —C(O)—OH, —C(O)—O—CH3, —CN, —NH2, —NH—C(O)—CH3, —NH—SO2—CH3, —N—(CH3)2, —SO2—NH2, —OH, —O—CH2—(CHF2), —S—CH3, —S(O)—CH3, —S(O)2—CH3 and bromine; and R2 and R2'are independently selected from the group consisting of hydrogen, chlorine, fluorine, methoxy, methyl, bromine, —C(O)—OH, —C(O)—O—CH3, —CN, —NH2, —NH—C(O)—CH3, —NH—SO2—CH3, —N—(CH3)2, —SO2—NH2, —OH, —O—CH2—(CHF2), —S—CH3, —S(O)—CH3 and —S(O)2—CH3; or R1 and R2, R2 and R3, R1' and R2', or R2'and R3', together with the two carbon atoms of ring1 or ring2 to which R1 and R2, R2 and R3, R1' and R2', or R2'and R3' are attached, form a dioxolane, dihydrofuran or furan ring, and any R1, R2, R3, R1', R2', or R3' that are not a member of said dioxolane, dihydrofuran or furan ring are the same as defined in the first part of this paragraph.

The invention furthermore relates to the composition and the use of compounds of formula I where R1, R3, R1', and R3'are independently selected from the group consisting of hydrogen, —(C1–C4)-alkyl, in which alkyl is substituted once, twice or three times by halogen, and —O—(C1–C4)-alkyl, in which alkyl is substituted once, twice or three times by halogen, and R2 and R2' are independently selected from the group consisting of hydrogen, halogen, —O—(C1–C4)-alkyl, and —(C1–C4)-alkyl; or R1 and R2, R2 and R3, R1' and R2', or R2' and R3', together with the two carbon atoms of ring1 or ring2 to which R1 and R2, R2 and R3, R1'and R2', or R2'and R3' are attached, form a 5- or 6-membered ring which is aromatic or saturated and contains zero, one or two heteroatoms which are independently selected from the group consisting of oxygen, nitrogen and sulfur, and any R1, R2, R3, R1', R2', or R3' that is not a member of said a 5- or 6-membered ring are independently selected from the group consisting of hydrogen, halogen, —(C1–C4)-alkyl, in which alkyl is unsubstituted or substituted once, twice or three times by halogen, and —O—(C1–C4)-alkyl, in which alkyl is unsubstituted or substituted once, twice or three times by halogen.

The invention furthermore relates to the composition and the use of compounds of formula I where R1, R3, R1', and R3'are independently selected from the group consisting of hydrogen and trifluoromethyl, and R2 and R2' are independently selected from the group consisting of hydrogen, chlorine, fluorine, methoxy and methyl; or R1 and R2, R2 and R3, R1' and R2', or R2'and R3', together with the two carbon atoms of ring1 or ring2 to which R1 and R2, R2 and R3, R1' and R2', or R2'and R3' are attached, form a dioxolane, dihydrofuran or furan ring, and any R1, R2, R3, R1', R2', or R3' that are not a member of said dioxolane, dihydrofuran or furan ring are independently selected from the group consisting of hydrogen, chlorine, fluorine, trifluoromethyl, methoxy, and methyl.

The present invention furthermore encompasses any related chemical entities of the compounds defined in the preceding paragraphs.

The term halogen is understood as meaning fluorine, chlorine, bromine or iodine.

The term —(C1–C4)-alkyl Is understood as meaning an alkyl that contains from 1 to 4 carbon atoms; for example methyl, ethyl, propyl, i-propyl, butyl or tertiary butyl.

a 5- or 6-membered ring which is aromatic or saturated and contains zero, one or two heteroatoms which are independently selected from the group consisting of oxygen, nitrogen or sulfur is exemplified by, but not limited to, the ring contained in dioxolane, pyrrole, pyrrolidine, pyridine, piperidine, tetrahydropyridine, pyrazole, imidazole, pyrazoline, imidazoline, pyrazolidine, imidazolidine, pyridazine, pyrimidine, pyrazine, piperazine, pyran, furan, dihydrofuran, tetrahydrofuran, oxazole, isoxazole, 2-isoxazoline, isoxazolidine, morpholine, oxothiolane, thiopyran, thiazole, isothiazole, 2-isothiazoline, isothiazolidine or thiomorpholine.

As used in this application, the term a related chemical entity of a compound is understood as meaning any stereoisomeric form of the compound, any mixture of two or more stereoisomeric forms of the compound, or any physiologically tolerated salt of the compound.

DETAILED DESCRIPTION OF PARTICULAR EMBODIMENTS

The compounds of formula I wherein R1', R2' and R3' are the same as R1, R2 and R3, respectively, can be prepared, for example, by reacting a compound of formula II

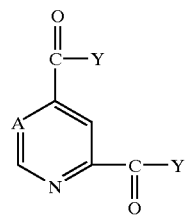
(II)

with a compound of formula III

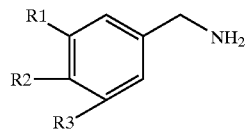
(III)

wherein R1, R2 and R3 have the meanings given in claim 1 and Y is halogen, hydroxyl or —(C1–C4)-alkoxy or, together with the carbonyl group to which Y is attached, forms an active ester or a mixed anhydride, to afford a compound of formula I as defined in claim 1 wherein R1', R2' and R3' are the same as R1, R2 and R3, respectively.

The compounds of formula I wherein R1', R2' and R3' are different from R1, R2 and R3, respectively, can be prepared, for example, by:

reacting a compound of formula II

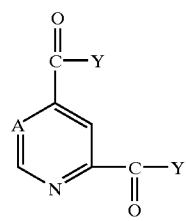
(II)

with a compound of formula III

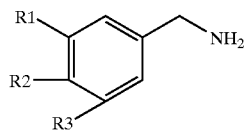
(III)

wherein R1, R2 and R3 have the meanings given in claim 1 and Y is halogen, hydroxyl or —(C1–C4)-alkoxy or, together with the carbonyl group to which Y is attached, forms an active ester or a mixed anhydride, to afford an intermediate compound of formula IV

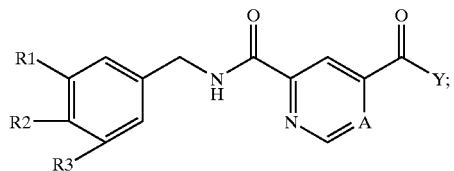
(IV)

and reacting said intermediate compound of formula IV with a compound of formula V wherein R1', R2' and R3' have the meanings given in claim 1

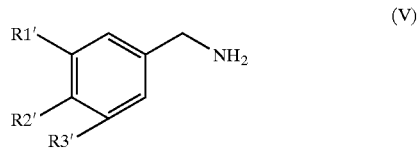
(V)

to afford a compound of formula I as defined in claim 1.

In that which follows, the preparation of compounds according to formula I and the preparation of the starting substances, which are required for this purpose, insofar as they are not commercially available, are described in more detail.

The compounds according to the invention are prepared in the simplest manner by mixing together the two components, i.e. the pyrimidine or pyridine derivative according to formula (II) and the amine according to formula III in equimolar quantities or in up to about a 5-fold excess of III and reacting them at temperatures of between −30° C. and 150° C., preferably at from 20° C. up to 100° C., until the reaction has come to an end. When the compound of formula IV is being prepared, the amine according to III is admixed up to an equimolar quantity of the compound of formula IIIa or IIIb and reacted as above. The completion of the reaction can be determined, for example, with the aid of thin layer chromatography or HPLC-MS. A variant of this process is that the reaction is carried out in a suitable solvent, such as diethyl ether, dimethoxyethane or tetrahydrofuran, chlorinated hydrocarbons such as methylene chloride, chloroform or tri- or tetrachloroethylene, benzene or toluene, or else polar solvents such as dimethylformamide, acetone or dimethyl sulfoxide. In this case, too, it is possible to use an excess of amine according to formula III, which excess can amount to up to about 5-fold quantities. The reaction temperatures in this case are between room temperature and the boiling point of the solvent, with temperatures in the range from room temperature up to 130° C. being particularly preferred.

The reaction can also take place by way of a mixed anhydride such as ethyl chloroformate or by way of an active ester such as paranitrophenyl ester (Y=ClCH2—COO or NO2—C6H4—O). Corresponding methods are known and described in the literature.

Where appropriate, the products, in particular the compound of formula IV; can be worked up, for example, by extraction or chromatography, for example through silica gel. The isolated product can be recrystallized and, where appropriate, converted into a physiologically tolerated salt using a suitable acid. Examples of suitable acids, which come into consideration are:mineral acids, such as hydrochloric acid and hydrobromic acid and also sulfuric acid, phosphoric acid, nitric acid or perchloric acid, or organic acids, such as formic acid, acetic acid, propionic acid, succinic acid, glycolic acid, lactic acid, malic acid, tartaric acid, citric acid, maleic acid, fumaric acid, phenylacetic acid, benzoic acid, methanesulfonic acid, toluenesulfonic acid, oxalic acid, 4-aminobenzoic acid, naphthalene-1,5-disulfonic acid or ascorbic acid.

Insofar as they are not commercially available, the starting compounds of formula III can be readily synthesized (e.g. Organikum, Organisch Chemisches Grundpraktikum [Organikum, Basic Practical Course in Organic Chemistry], 15th edtn., VEB Deutscher Verlag der Wissenschaften [VEB German Publishing Company for the Sciences], 1976;

an overview of the various options can be found in the methods index, p. 822).

The starting compounds of formula (II) can be obtained, for example, by converting pyrimidine-4,6-dicarboxylic acid or pyridine-2,4-dicarboxylic acid, respectively, into the corresponding pyrimidine-4,6-dicarbonyl halide, or, respectively, pyridine-2,4-dicarbonyl halide, preferably chloride (using methods known from the literature), preferably in the presence of a catalyst such as dimethylformamide. This acid halide can then be reacted, for example, either with a suitable alcohol, e.g. paranitrobenzyl alcohol, to give the corresponding active ester or else with lower alcohols, such as methanol or ethanol, to give the corresponding esters. The pyrimidine-4,6-dicarboxylic acid can also initially be converted, in the added presence of a suitable carboxylic acid or of a carboxylic ester, such as ethyl chloroformate, into a mixed anhydride, which is then reacted with the amines of the compound of formulae III and IV to give the products according to the invention. An appropriate method is also described in the literature.

The pyrimidine-4,6-dicarboxylic acid is prepared using methods known from the literature, for example by oxidizing 4,6-dimethylpyrimidine, which, for its part, can be obtained, for example, by catalytically hydrogenating commercially obtainable 2-mercapto-4,6-dimethylpyrimidine.

Insofar as compounds of formula I permit diastereoisomeric or enantiomeric forms, and accrue as their mixtures in connection with the chosen synthesis, the separation into the pure stereoisomers is achieved either by chromatography on an optionally chiral support material or, insofar as the racemic compound of formula is capable of sulfonation, by fractional crystallization of the diastereomeric salts which are formed using an optically active base or acid as auxiliary substance. Examples of suitable chiral stationary phases for the thin-layer-chromatographic or column-chromatographic separation of enantiomers are modified silica gel supports (what are termed Pirkle phases) and also high molecular weight carbohydrates such as triacetylcellulose. Gas-chromatographic methods on chiral stationary phases can also be used for analytical purposes following appropriate derivatization, as known to the skilled person. In order to separate the racemic carboxylic acids into their enantiomers, the differently soluble diastereomeric salts are formed using an optically active base which can as a rule be obtained commercially, such as (−)-nicotine, (+)- and (−)-phenylethylamine, quinine bases, L-lysine or L- and D-arginine, the more difficulty soluble component is then isolated as a solid, the more readily soluble diastereomer is separated off from the mother liquor, and the pure enantiomers are then isolated from the diastereomeric salts which had been obtained in this way. The racemic compounds of formula I which contain a basic group such as an amino group can in principle be converted into the pure enantiomers in the same way using optically active acids, such as (+)-camphor-10-sulfonic acid, D- and L-tartaric acid, D- and L-lactic acid and also (+) and (−)-mandelic acid. Chiral compounds which contain alcohol or amine functions can also be converted Into the corresponding esters or amides using appropriately activated or optionally N-protected enantiomerically pure amino acids or, conversely, chiral carboxylic acids can be converted into the amides using carboxy-protected enantiomerically pure amino acids or into the corresponding chiral esters using enantiomerically pure hydroxycarboxylic acids such as lactic acid. The chirality of the amino acid radical or alcohol radical which has been introduced in enantiomerically pure form can then be used for separating the isomers by means of separating the diastereomers, which are now present, by crystallization or chromatography on suitable stationary phases and, after that, once again eliminating the entrained chiral molecular moiety using suitable methods.

Acidic or basic products of the compound of formula I can be present in the form of their salts or in free form. Preference is given to pharmacologically tolerated salts, for example alkali metal salts or alkaline earth metal salts or hydrochlorides, hydrobromides, sulfates, hemisulfates, all the possible phosphates, and also salts of the amino acids, natural bases or carboxylic acids.

Physiologically tolerated salts are prepared in a manner known per se from compounds of formula I, including their stereoisomeric forms, which are capable of salt formation. The carboxylic acids form stable alkali metal salts, alkaline earth metal salts or, where appropriate, substituted ammonium salts with basic reagents such as hydroxides, carbonates, hydrogen carbonates, alcoholates and ammonia or organic bases, for example trimethylamine or triethylamine, ethanolamine or triethanolamine, or else basic amino acids, for example lysine, ornithine or arginine. Insofar as the compounds of formula I possess basic groups, stable acid addition salts can also be prepared using strong acids. Both inorganic and organic acids, such as hydrochloric acid, hydrobromic acid, sulfuric acid, phosphoric acid, methanesulfonic acid, benzenesulfonic acid, p-toluenesulfonic acid, 4-bromobenzenesulfonic acid, cyclohexylamidosulfonic acid, trifluoromethylsulfonic acid, acetic acid, oxalic acid, tartaric acid, succinic acid or trifluoroacetic acid, are suitable for this purpose.

Because of their pharmacological properties, the compounds of formula I are suitable for the prophylaxis and therapy of all those diseases whose course involves an increased activity of matrix metalloproteinase 13.

These diseases include degenerative joint diseases such as osteoarthroses, spondyloses, chondrolysis following joint trauma or a relatively long period of joint immobilization following injuries to the meniscus or patella or the tearing of a ligament. In addition, they also include diseases of the connective tissue such as collagenoses, periodontal diseases, wound healing disturbances and chronic diseases of the locomotor system, such as inflammatory, immunologically or metabolism-determined acute and chronic arthritides, arthropathies, myalgias and disturbances of bone metabolism or cancer diseases such as breast cancer.

The pharmaceuticals according to the invention can be administered by subcutaneous, intraarticular, intraperitoneal or intravenous injection intraarticular injection is preferred. It is also possible to administer them rectally, orally, by inhalation or transdermally.

The invention also relates to a process for producing a pharmaceutical, in which process at least one compound of formula I is brought, together with a pharmaceutically suitable and physiologically tolerated excipient and, where appropriate, further suitable active compounds, additives or auxiliary substances, into a suitable form for administration.

The compounds of formula I are mixed with the additives which are suitable for this purpose, such as carrier substances, stabilizers or inert diluents and brought, using the customary methods, into suitable administration forms, such as tablets, sugar-coated tablets, hard gelatin capsules, aqueous alcoholic or oily suspensions or aqueous or oily solutions. Examples of inert carrier substances which can be used are gum arabic, magnesium oxide, magnesium carbonate, potassium phosphate, lactose, glucose or starch, in particular corn starch. In this connection, the preparation can also be effected as dry granules or wet granules. Examples of suitable oily carrier substances or solvents are vegetable or animal oils, such as sunflower oil or cod liver oil.

For the purpose of subcutaneous, intraarticular, intraperitoneal or intravenous administration, the active compounds are, if desired, brought into solution, suspension or emulsion using the substances which are suitable for this purpose, such as solubilizers, emulsifiers or other auxiliary substances. Examples of suitable solvents are physiological sodium chloride solution or alcohols, for example ethanol, propanol or glycerol, and, in addition, sugar solutions, such as glucose or mannitol solutions, or else a mixture of the different solvents which have been mentioned.

In addition, use is made of customary adjuvants, such as carrier substances, disintegrants; binders, coating agents, swelling agents, glidants, lubricants, flavorants, sweeteners and solubilizers. Frequently employed auxiliary substances which may be mentioned are magnesium carbonate, titanium dioxide, lactose, mannitol and other sugars, talc, milk protein, gelatin, starch, cellulose and its derivatives, animal and vegetable oils, such as cod liver oil, sunflower oil, peanut oil or sesame oil, polyethylene glycol and solvents such as sterile water and monohydric or polyhydric alcohols, such as glycerol.

The compounds of formula I are preferably produced and administered as pharmaceutical preparations in dosage units, with each unit containing, as the active constituent, a particular dose of the compound of formula 1. For this purpose, they can be administered orally in doses of from 0.01 mg/kg/day to 25.0 mg/kg/day, preferably of from 0.01 mg/kg/day to 5.0 mg/kg/day, or parenterally in doses of from 0.001 mg/kg/day to S mg/kg/day, preferably of from 0.001 mg/kg/day to 2.5 mg/kg/day. The dose can also be increased in severe cases. However, relatively small doses suffice in many cases. These figures relate to the treatment of an adult patient.

The invention is explained below with the aid of examples.

EXAMPLE 1

Pyrimidine-4,6-dicarboxylic Acid Dibenzylamide 1.7 g of pyrimidine-4,6-dicarboxylic acid are suspended in 20 ml of toluene and 2.4 g of thionyl chloride and 0.2 ml of dimethylformamide are added. The mixture is heated to reflux until it is no longer possible to observe any gas evolution (about 3 hours (h)). About 5 ml of solvent are distilled off and the mixture is then cooled down to from 0 C to 10° C. and 2.7 g of benzylamine, dissolved in 10 ml of toluene, are added. The solution is slowly heated to room temperature, then stirred at room temperature for 12 hours and evaporated down to dryness. The residue is taken up in 50 ml of methylene chloride and the solution is extracted 3 times by shaking with saturated sodium hydrogen carbonate solution; the organic phase is washed with water, dried with magnesium sulfate and evaporated.

The solid is recrystallized from diisopropyl ether. Yield: 2.1 m.p.: 131 C to 132° C.

EXAMPLE 2

Pyrimidine-4,6-dicarboxylic acid bis(3-chloro-4-fluorobenzylamide)

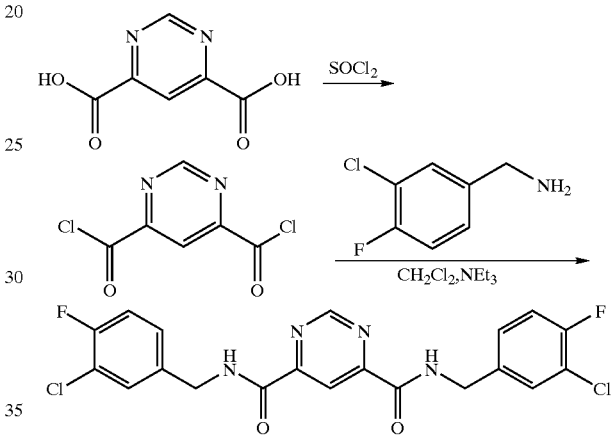

200 mg (1.2 mmol) of pyrimidine-4,6-dicarboxylic acid were suspended in 0.3 ml (4.1 mmol) of thionyl chloride. This mixture was heated at 85° C. for 2 h while being stirred. After it had been cooled down to room temperature, 2 ml of absolute dichloroethane were added. The suspension was cooled down to 0° C. and 0.33 ml (2.4 mmol) of triethylamine was added. 861 mg(5.4 mmol) of 3-chloro-4-fluorobenzylamine were added while stirring vigorously.

The mixture was then stirred for further 15 minutes. It was then diluted with 10 ml of dichloromethane after which 10 ml of water were added. After 5 minutes, the mixture was transferred into a separating funnel and the phases were separated. The organic phase was washed twice with saturated sodium chloride solution and then dried over magnesium sulfate. After filtration, the filtrate was concentrated under reduced pressure and the residue which was obtained in this way was dissolved in ethyl acetate. The product was crystallized from the solution by adding heptane. Beige-colored flakes were obtained and were dried under reduced pressure. Yield: 263 mg (49%).

The following compounds were prepared in analogy with example 2.

TABLE 1

| Example | Structure | MS (ESI+) |
|---|---|---|
| 3 | 4-Cl-C6H4-CH2-NHC(O)-pyrimidine-4,6-diyl-C(O)NH-CH2-C6H4-4-Cl | 415.13 |
| 4 | C6H5-CH2-NHC(O)-pyridine-2,4-diyl-C(O)NH-CH2-C6H5 · ClH | 346.27 |
| 5 | 4-CH3-C6H4-CH2-NHC(O)-pyrimidine-4,6-diyl-C(O)NH-CH2-C6H4-4-CH3 | 375.26 |
| 6 | 3-(OCF3)-C6H4-CH2-NHC(O)-pyrimidine-4,6-diyl-C(O)NH-CH2-C6H4-3-(OCF3) | 515.21 |
| 7 | 4-F-C6H4-CH2-NHC(O)-pyridine-2,4-diyl-C(O)NH-CH2-C6H4-4-F · HCOOH | 382.21 |
| 8 | 3-CH3-C6H4-CH2-NHC(O)-pyridine-2,4-diyl-C(O)NH-CH2-C6H4-3-CH3 · ClH | 374.25 |
| 9 | 4-OCH3-C6H4-CH2-NHC(O)-pyridine-2,4-diyl-C(O)NH-CH2-C6H4-4-OCH3 · HCOOH | 406.31 |
| 10 | 3,5-F2-C6H3-CH2-NHC(O)-pyrimidine-4,6-diyl-C(O)NH-CH2-C6H3-3,5-F2 | 419.22 |

TABLE 1-continued

| Example | Structure | MS (ESI+) |
|---|---|---|
| 11 | 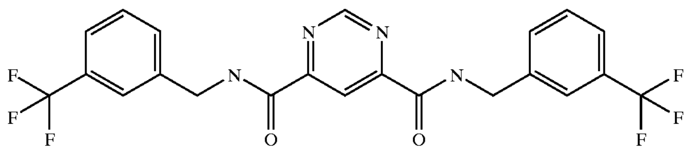 | 483.24 |
| 12 | 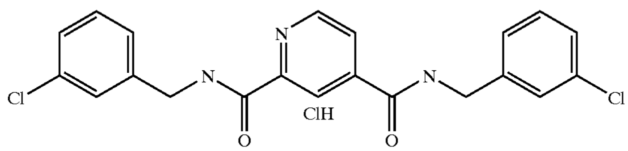 | 414.15 |
| 13 | 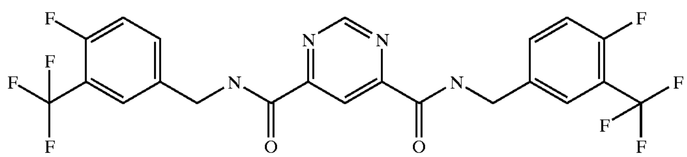 | 560.18 (M + MeCN) |
| 14 | 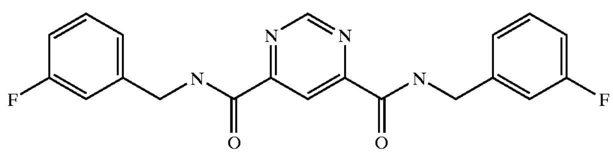 | 383.17 |
| 15 | 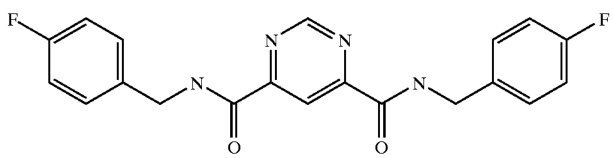 | 383.15 |
| 16 | 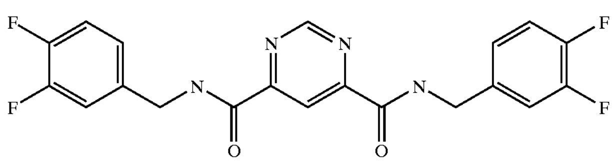 | 419.02 |
| 17 | 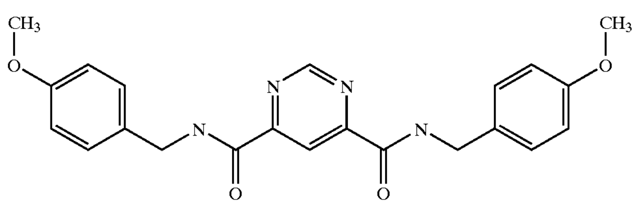 | 407.23 |
| 18 | 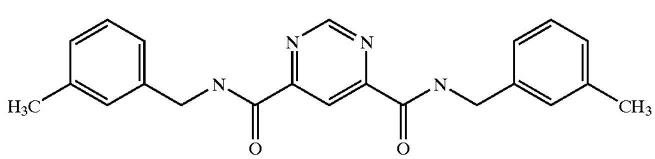 | 375.13 |
| 19 | 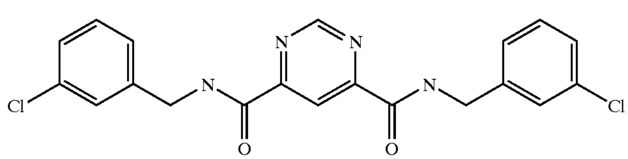 | 415.06 |

TABLE 1-continued

| Example | Structure | MS (ESI+) |
|---|---|---|
| 20 | 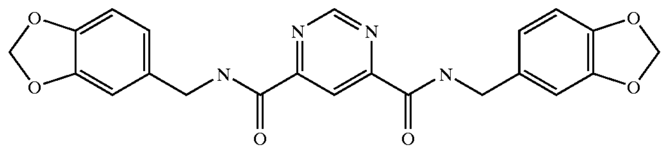 | 435.22 |
| 21 | 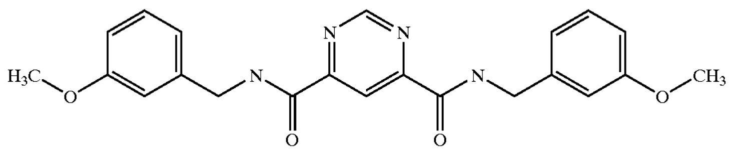 | 407.30 |
| 22 | 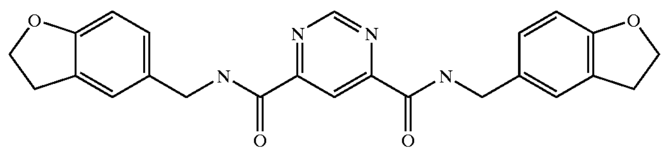 | 431.06 |
| 23 | 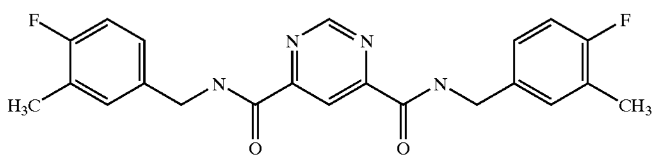 | 411.25 |

EXAMPLE 24

Dimethylpyrimidine-4,6-dicarboxylate 10 g (0.059 mol) of pyrimidine-4,6-dicarboxylic acid were suspended in 1.4 l of methanol, after which 10.93 ml (0.356 mol) of concentrated hydrochloric acid were added and the mixture was stirred under reflux (65° C.) for 3 hours (h). The reaction mixture was concentrated under reduced pressure after which the residue was taken up once again in methanol; the mixture was filtered and the resulting solution was concentrated.

Yield 11.02 g (94.4%) MS (ES$^+$): m/e=197.20.

2.55 g (0.01299 mol) of the resulting compound dimethylpyrimidine-4,6-dicarboxylate were dissolved in 100 ml of dimethylformamide (DMF), after which 1.42 ml (0.01299 mol) of benzylamine were added and the mixture was heated to 50° C. After 4 hours, the solution is concentrated under reduced pressure. The residue is chromatographed through a 500 ml silica gel column using heptane/ethyl acetate (1:1). Fractions containing the compound methyl-6-benzylcarbamoylpyrimidine-4-carboxylate were concentrated. Yield 1.268 g (36%) MS (ES$^+$): m/e=272.20.

200 mg (0.737 mmol) of the resulting compound methyl-6-benzylcarbamoylwere dissolved in 4 ml of DMF, after which 225.98 mg (1.29 mmol) of 3-trifluoromethylbenzylamine were added and the mixture was stirred at 50° C. for 1 day. After that, the solution was concentrated under reduced pressure. The residue was purified by means of preparative HPLC (water/acetonitrile gradient, Purospher RP18). Fractions containing pyrimidine-4,6-dicarboxylic acid 4-benzylamide-6-(3-trifluoromethylbenzylamide) were concentrated under reduced pressure and freeze-dried.

Yield: 240 mg (79%) MS (ES): m/e=415.27.

The following compounds were prepared in an analogous manner

TABLE 2

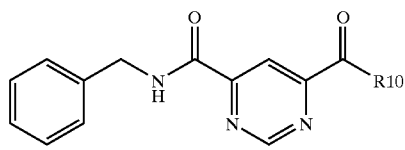

| Example | R10 radical | MS (ES$^+$): m/e |
|---|---|---|
| 25 | 3-fluorobenzylamine | 365.23 |
| 26 | 4-fluorobenzylamine | 365.23 |
| 27 | 3,4-difluorobenzylamine | 383.27 |
| 28 | 4-methoxybenzylamine | 377.28 |
| 29 | 3-methylbenzylamine | 361.28 |
| 30 | 3-chlorobenzylamine | 381.23 |

The following compounds were prepared in analogy with example 1 to 30.

TABLE 3

| Example | Structure | MS (ESI+) |
|---------|-----------|-----------|
| 31 | 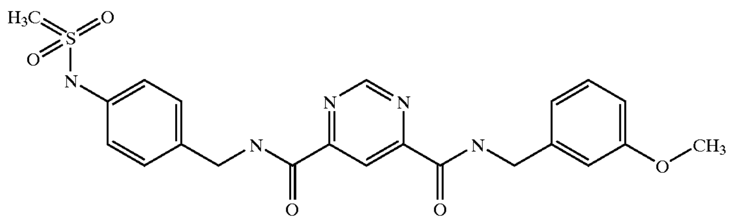 | 470.22 ES+ |
| 32 | 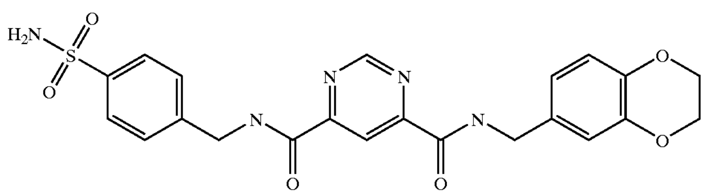 | 484.12 ES+ |
| 33 | 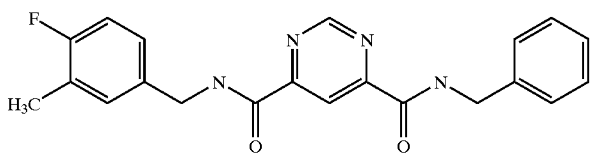 | 378.15 ES+ |
| 34 | 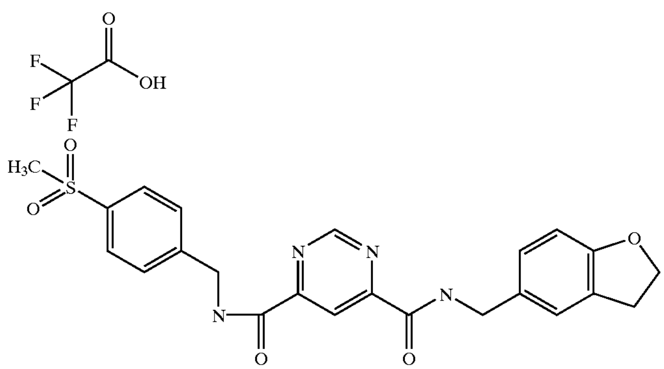 | 466.13 ES+ |
| 35 | 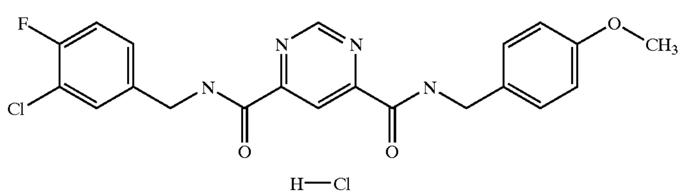 | 429.17 ES+ |
| 36 | 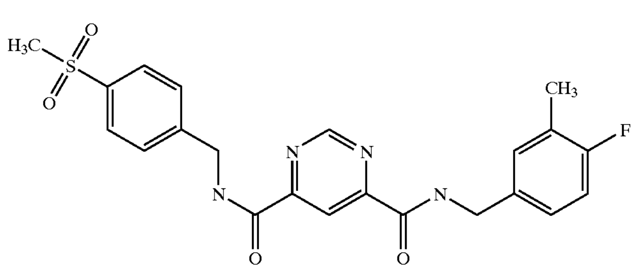 | 456.13 ES+ |

TABLE 3-continued

| Example | Structure | MS (ESI+) |
|---|---|---|
| 37 | 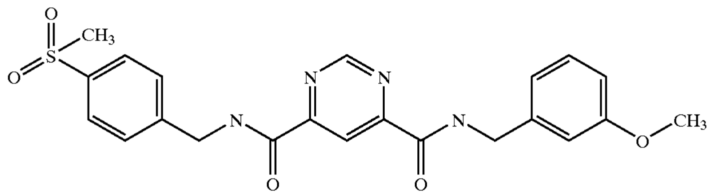 | 455.10 ES+ |
| 38 | 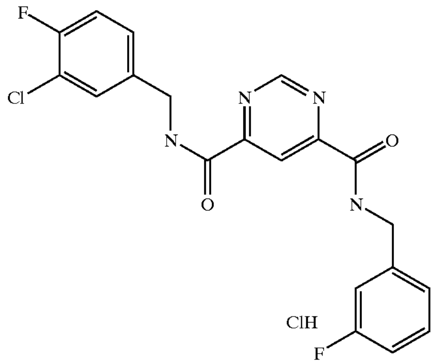 | 417.11 ES+ |
| 39 | 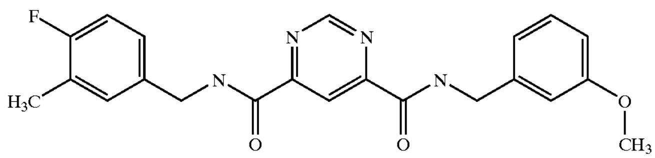 | 409.28 ES+ |
| 40 | 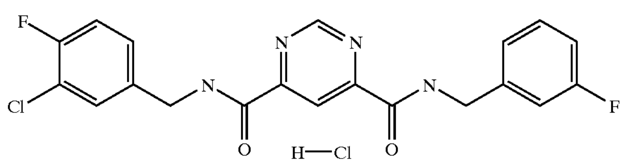 | 417.11 ES+ |
| 41 | 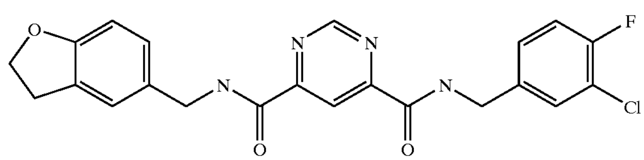 | 441.25 |
| 42 | 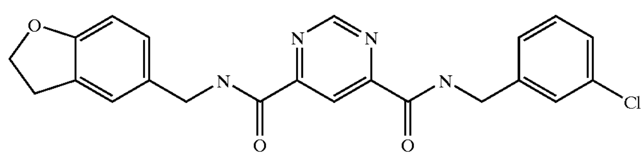 | 423.26 |
| 43 | 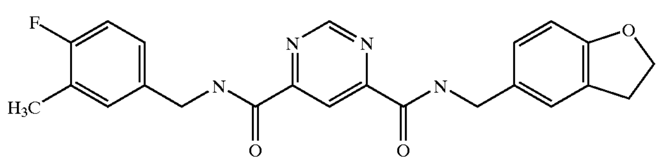 | 421.29 ES+ |
| 44 | 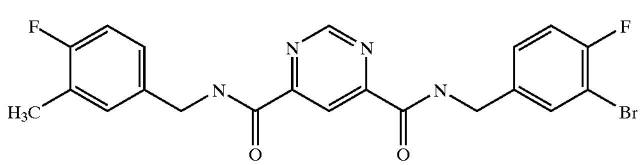 | 477.15 ES+ |

TABLE 3-continued

| Example | Structure | MS (ESI+) |
|---------|-----------|-----------|
| 45 | 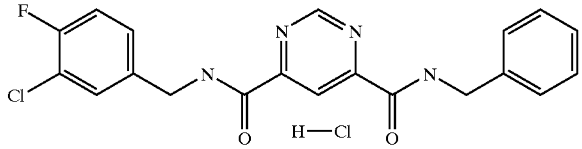 | 399.20 ES+ |
| 46 | 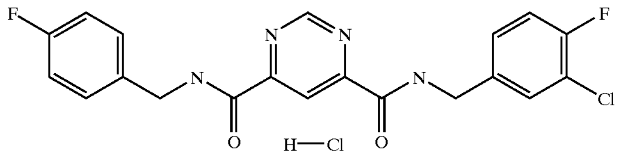 | 417.16 ES+ |
| 47 | 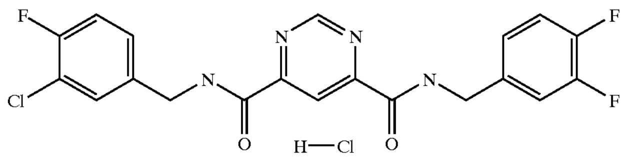 | 435.14 ES+ |
| 48 | 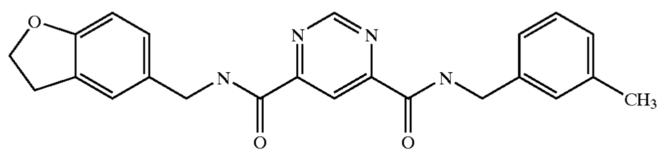 | 403.31 ES+ |
| 49 | 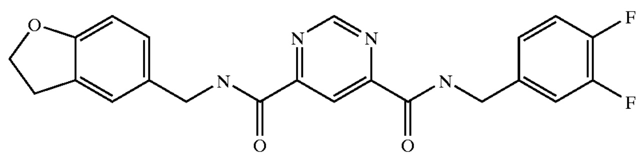 | 425.30 ES+ |
| 50 | 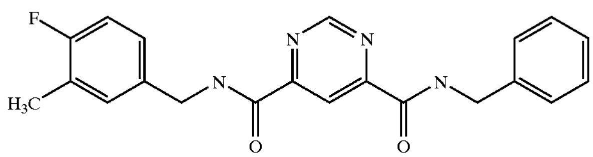 | 379.29 ES+ |
| 51 | 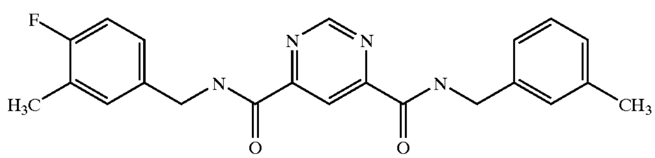 | 393.33 ES+ |
| 52 | 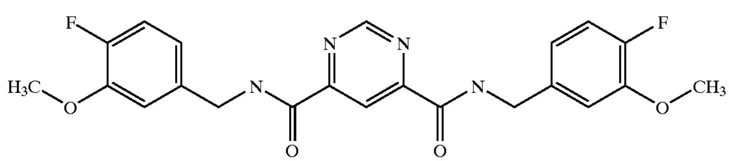 | 443.28 ES+ |
| 53 | 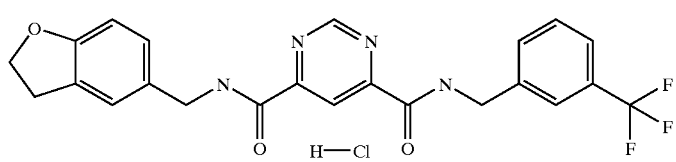 | 457.20 ES+ |

TABLE 3-continued

| Example | Structure | MS (ESI+) |
|---------|-----------|-----------|
| 54 | 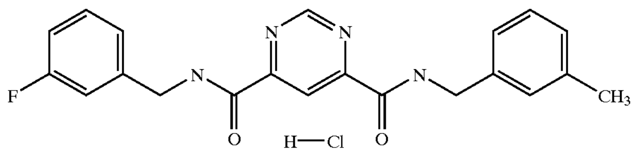 | 379.19 ES+ |
| 55 | 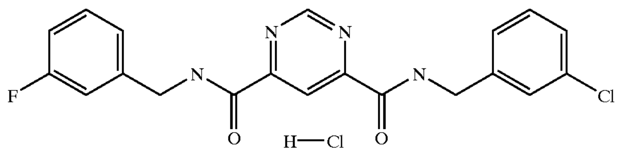 | 399.14 ES+ |
| 56 | 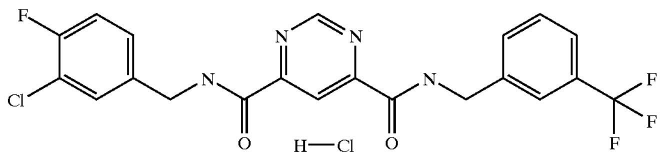 | 467.17 ES+ |
| 57 | 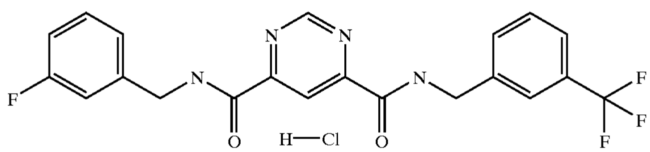 | 433.24 ES+ |
| 58 | 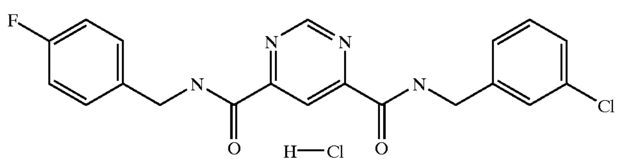 | 399.18 ES+ |
| 59 | 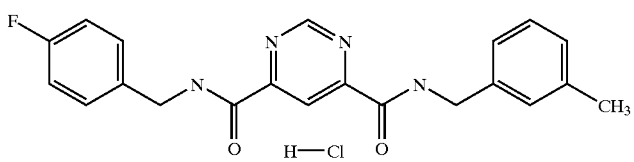 | 379.10 ES+ |
| 60 | 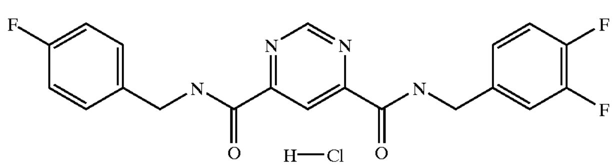 | 401.05 ES+ |
| 61 | 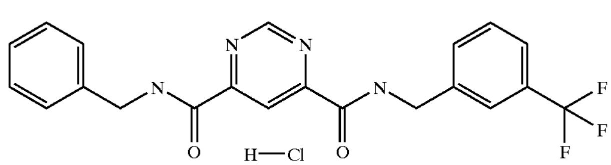 | 415.27 ES+ |
| 62 | 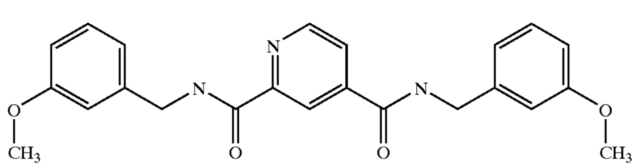 | 406.26 ES+ |

TABLE 3-continued

| Example | Structure | MS (ESI+) |
|---|---|---|
| 63 | 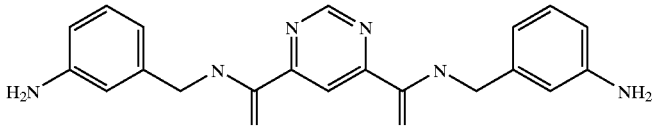 | 377.32 ES+ |
| 64 | 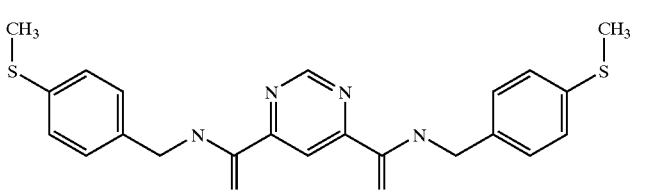 | 439.21 ES+ |
| 65 | 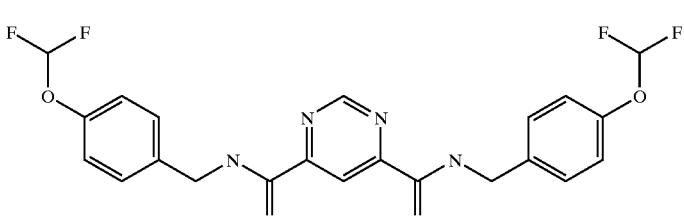 | 479.18 ES+ |
| 66 | 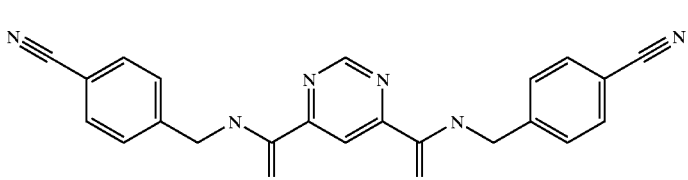 | 397.21 ES+ |
| 67 | 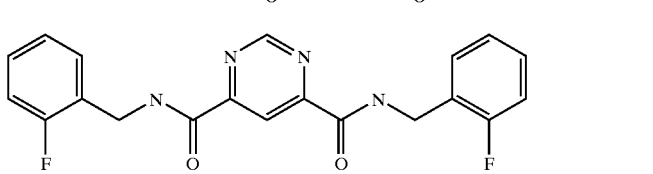 | 383.27 ES+ |

PHARMACOLOGICAL EXAMPLES

Determining the enzymic activity of the catalytic domain of human collagenase-3 (MMP-13).

This protein is obtained as an inactive proenzyme from INVITEK, Berlin (catalog No. 30 100 803). Activation of the proenzyme:

2 parts by volume of proenzyme are incubated with 1 part by volume of APMA solution at 37° C. for 1.5 hours. The APMA solution is prepared from a 10 mmol/l solution of p-aminophenylmercuric acetate in 0.1 mmol/l NaOH by diluting it with 3 parts by volume of Tris/HCl buffer, pH 7.5 (see below). The pH is adjusted to between 7.0 and 7.5 by adding 1 mmol/l HCl. After the enzyme has been activated, it is diluted with the Tris/HCl buffer down to a concentration of 1.67 µg/ml.

In order to measure the enzyme activity, 10 µl of enzyme solution are incubated for 15 minutes with 10 µl of a buffered 3% (v/v) solution of dimethyl sulfoxide (reaction 1). In order to measure the enzyme inhibitor activity, 10 µl of enzyme solution are incubated with 10 µl of a buffered 3% (v/v) solution of dimethyl sulfoxide which contains the enzyme inhibitor (reaction 2).

Both in reaction 1 and in reaction 2, the enzyme reaction is monitored by fluorescence spectroscopy (328 nm (extinction)/393 nm (emission)) after 10 µl of a 3% (v/v) aqueous solution of dimethyl sulfoxide containing 0.75 mmol of the substrate/l have been added.

The enzyme activity is presented as increase in extinction/minute.

The inhibitor effect is calculated as percentage inhibition in accordance with the following formula:

% inhibition=100−[(increase in extinction/minute in reaction 2)/(increase in extinction/minute in reaction 1)×100].

The $IC_{50}$, i.e. the concentration of inhibitor which is required for a 50% inhibition of the enzyme activity, is determined graphically by plotting the percentage inhibitions at different inhibitor concentrations.

The buffer solution contains 0.05% Brij (Sigma, Deisenhofen, Germany) and also 0.1 mol of Tris/HCl/l, 0.1 mol of NaCl/l and 0.01 mol of $CaCl_2$/l (pH=7.5).

The enzyme solution contains 1.67 µg of the enzyme domain/ml.

The substrate solution contains 0.75 mmol of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-$NH_2$/l(Bachem, Heidelberg, Germany).

The following table 4 shows the results.

TABLE 4

| Example | IC50 MMP13 (nM) | Example | IC50 MMP13 (nM) | Example | IC50 MMP13 (nM) |
|---|---|---|---|---|---|
| 1 | 400 | 9 | 320 | 17 | 80 |
| 2 | 23 | 10 | 300 | 18 | 72 |
| 3 | 5600 | 11 | 300 | 19 | 57 |
| 4 | 3400 | 12 | 260 | 20 | 14 |
| 5 | 2000 | 13 | 210 | 21 | 10 |
| 6 | 700 | 14 | 200 | 22 | 9 |
| 7 | 620 | 15 | 190 | 23 | 8 |
| 8 | 400 | 16 | 105 | | |

COMPARATIVE EXAMPLE

The compound pyrimidine-4,6-dicarboxylic acid diethylamide was prepared as described in EP 041 8797. A value of 90 000 nM was obtained when the IC value for the inhibition of human collagenase-13 (MMP-13) was determined as described in the above example. This compound therefore has practically no inhibitory effect on MMP 13.

Determining the enzymic activity of the catalytic domains of human neutrophil collagenase (MMP-8) and human stromelysin (MMP-3).

The enzymes human neutrophil collagenase and human stromelysin were prepared as active catalytic domains as described in Weithmann et al Inflamm Res, 46 (1997), pages 246–252. The measurement of the activity of the enzymes, and the determination of the inhibitory effect of inhbitors on the activity of the enzymes, were also carried out as described in that publication.

The compounds according to the abovementioned examples 1 to 67 in each case exhibited $IC_{50}$ values of more than 100 nM when determining human neutrophil collagenase and human stromelysin. These compounds therefore have practically no inhibitory effect on MMP 3 and MMP 8.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

We claim:

1. A compound of formula 1:

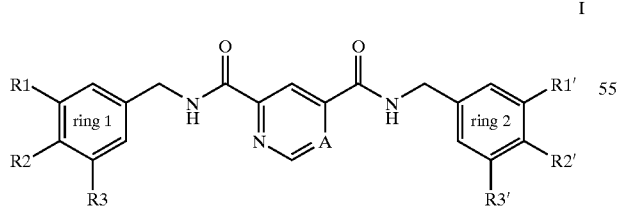

I wherein

A is a nitrogen atom;

R1 and R3 are independently selected from the group consisting of hydrogen, halogen, —($C_1$–$C_4$)-alkyl, in which alkyl is unsubstituted or substituted once, twice or three times by halogen, —O—($C_1$–$C_4$)-alkyl, in which alkyl is =unsubstituted or substituted once, twice or three times by halogen,

—C(O)—O—R4,

—CN,

—N(R5)—(R6)

—OH,

—S—($C_1$–$C_4$)-alkyl,

—S(O)($C_1$–$C_4$)-alkyl and,

—S(O)$_2$—R7, and

R2 is selected from the group consisting of hydrogen, halogen,

—($C_1$–$C_4$alkyl,

—O—($C_1$–$C_4$)-alkyl,

—C(O)—O—R4,

—CN,

—N(R5)-(R6),

—OH,

—S—($C_1$–$C_4$)-alkyl,

—S(O)—($C_1$–$C_4$)alkyl and,

—S(O)$_2$—R7; or R1 and R2, taken together with the two carbon atoms of ring1 to which R1 and R2 are attached, form a 5- or 6-membered ring which is aromatic or saturated and contains zero, one or two heteroatoms which are independently oxygen, nitrogen and sulfur while R3 is as defied above; or R2 and R3, taken together with the two carbon atoms of ring1 to which R2 and R3 are attached, form a 5- or 6-membered ring which is aromatic or saturated and contains zero, one or two heteroatoms which are independently oxygen, nitrogen and sulfur while R1 is not part of a ring and is as defined above, R1' and R3' are independently selected from the group consisting of hydrogen, halogen, —($C_1$–$C_4$)-alkyl, in which alkyl is unsubstituted or substituted once, twice or three times by halogen, —O—($C_1$–$C_4$alkyl, in which alkyl is unsubstituted or substituted once, twice or three times by halogen,

—C(O)—O—R4,

—CN,

—N(R5)-(R6),

—OH,

—S—($C_1$–$C_4$)-alkyl,

—S(O)—($C_1$–$C_4$)alkyl and

—S(O)$_2$—R7, and

R2' is selected from the group consisting of hydrogen, halogen,

—($C_1$–$C_4$)-alkyl,
—O—($C_1$–$C_4$)-alkyl,
—C(O)—O—R4,
—CN,
—N(R5)-(R6),
—OH,
—S—($C_1$–$C_4$)-alkyl,
—S(O)—($C_1$–$C_4$)-alkyl and
—S(O)$_2$—R7; or R1' and R2', taken together with the two carbon atoms of ring2 to which R1' and R2'are attached, form a 5- or 6-membered ring which is aromatic or saturated and contains zero, one or two heteroatoms which are independently oxygen, nitrogen and sulfur while R3' is as defined above; or R2' and R3', taken together with the two carbon atoms of ring2 to which R2' and R3' are attached, form a 5- or 6-membered ring which is aromatic or saturated and contains zero, one or two heteroatoms which are independently selected from the group consisting of oxygen, nitrogen and sulfur while R1' is not a number of a ring and is as defined above, R4 is hydrogen or —($C_1$–$C_4$)alkyl;

R5 and R6 are independently selected from the group consisting of hydrogen;
—(C1–C4)-alkyl,
—C(O)—(C1–C4)-alkyl and,
—SO2-(C1–C4)-alkyl, and R7 is selected from the group consisting of
—(C1–C4)-alkyl,
—OH and,
—NH$_2$, a stereoisomeric form of the compound of formula I, a mixture of two or more stereoisomeric forms of the compound of formula I, or a physiologically tolerated salt of the compound of formula I, provided that at least one of the radicals R1, R2, R3, R1', R2', R3' is not selected from the group consisting of hydrogen, halogen, nitro, —(C1–C4)-alkyl and —O—(C1–C4)-alkyl.

2. A compound of claim 1, wherein R1, R3, R1', R3' are not selected from the group consisting of halogen, unsubstituted —(C1–C4)-alkyl and unsubstituted —O—($C_1$–$C_4$)-alkyl except when there is a 5- or 6-membered ring formed between R1 and R2, or between R2 and R3, or between R1' and R2', or between R2' and R3', then R1, R3, R1', R3' are the same as defined in claim 1.

3. A compound of claim 1, wherein R1, R3, R1', and R3' are independently selected from the group consisting of hydrogen, chlorine, fluorine, trifluoromethyl, methoxy, methyl, —C(O)—OH, —C(O)O—CH$_3$, —CN, —NH$_2$, —NH—CH$_3$, —NH—SO$_2$—CH$_3$, —N—(CH$_3$)$_2$, —SO$_2$—NH$_2$, —OH, —O—CH$_2$—(CHF$_2$), —S—CH$_3$, —S(O)—CH$_3$, —S(O)$_2$—CH$_3$ and bromine; and R2 and R2' are independently selected from the group consisting of hydrogen, chlorine, fluorine, methoxy, methyl, bromine, —C(O)—OH, —C(O)—O—CH$_3$, —CN, —NH$_2$, —NH—C—(O)—CH$_3$, —NH—SO$_2$—CH$_3$, —N—(CH$_3$)$_2$, —SO$_2$—NH$_2$, —OH, —O—CH$_2$—(CHF$_2$), —S—CH$_3$, S(O)CH$_3$ and —S(O)$_2$—CH$_3$; or R1 and R2, R2 and R3, R1'and R2', or R2'and R3', together with the two carbon atoms of ring1 or ring2 to which R1 and R2, R2 and R3, R1'and R2', or R2'and R3', respectively, are attached, form a dioxolane, dihydrofuran or furan ring, and any R1, R2, R3, R1', R2', or R3' that is not a member of said dioxolane, dihydrofuran or furan ring is the same as defined in the first part of this claim.

4. A compound of claim 1, wherein R1, R3, R1', and R3'are independently selected from the group consisting of hydrogen, —(C1–C4)-alkyl, in which alkyl is substituted once, twice or three times by halogen, and (C1–C4)-alkyl, in which alkyl is substituted once, twice or three times by halogen, and R2 and R2' are independently selected from the group consisting of hydrogen, halogen, —O—($C_1$–$C_4$)-alkyl, and —($C_1$–$C_4$)-alkyl; or R1 and R2, R2 and R3, R1' and R2', or R2' and R3', together with the two carbon atoms of ring1 or ring2 to which R1 and R2, R2 and R3, R1'and R2', or R2'and R3', respectively, are attached, form a 5- or 6-membered ring which is aromatic or saturated and contains zero, one or two heteroatoms which are independently selected from the group consisting of oxygen, nitrogen and sulfur, and any R1, R2, R3, R1', R2', or R3' that is not a member of said a 5- or 6-membered ring is independently selected from the group consisting of hydrogen, halogen, —($C_1$–$C_4$) alkyl, in which alkyl is unsubstituted or substituted once, twice or three times by halogen, and —O—($C_1$–$C_4$)-alkyl, in which alkyl is unsubstituted or substituted once, twice or three times by halogen.

5. A compound of claim 1, wherein R1, R3, R1', and R3' are independently selected from the group consisting of hydrogen and trifluoromethyl, and R2 and R2' are independently selected from the group consisting of hydrogen, chlorine, fluorine, methoxy and methyl; or R1 and R2, R and R3, R1' and R2', or R2'and R3', together with the two carbon atoms of ring1 or ring2 to which R1 and R2, R2 and R3, R1'and R2', or R2' and R3', respectively, are attached, form a dioxolane, dihydrofuran or furan ring, and any R1, R2, R3, R1', R2', or R3' that is not a member of said dioxolane, dihydrofuran or furan ring is independently selected from the group consisting of hydrogen, chlorine, fluorine, trifluoromethyl, methoxy, and methyl.

6. A process for preparing the compound of formula I as defined in claim 1, comprising:

reacting a compound of formula II

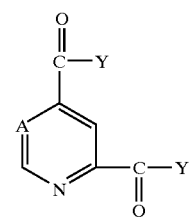

(II)

with a compound of formula III

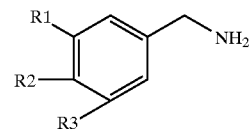

(III)

wherein R1, R2 and R3 have the meanings given in claim 1 and Y is halogen, hydroxyl or —($C_1$–$C_4$)alkoxy or, together with the carbonyl group to which Y is attached, forms an active ester or a mixed anhydride, to afford a compound of formula I defined in claim 1.

7. A process for preparing the compound of formula I as defined in claim 1, comprising:
reacting a compound of formula III

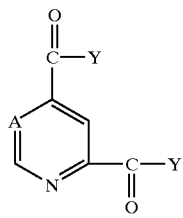
(II)

with a compound of formula III

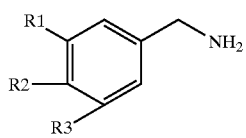
(III)

wherein R1, R2 and R3 have the meanings given in claim 1 and Y is halogen, hydroxyl or —(C$_1$–C$_4$)-alkoxy or, together with the carbonyl group to which Y is attached, forms an active ester or a mixed anhydride, to afford an intermediate compound of formula IV

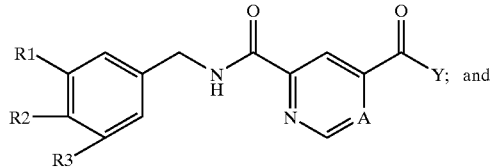
(IV)

reacting said intermediate compound of formula IV with a compound of formula III to afford a compound of formula I as defined in claim 1.

8. A pharmaceutical composition which comprises an effective amount of at least one compound of claim 1 together with a pharmaceutically suitable and physiologically tolerated carrier substance.

9. A method for therapy of a disease which is a degenerative joint disease or a disease of the connective tissue comprising administering a compound of formula I:

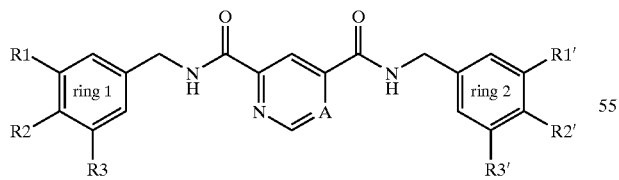
I wherein
A is a nitrogen atom;
R1 and R3 are independently selected from the group consisting of;
hydrogen,
halogen,
—(C$_1$–C$_4$)-alkyl, in which alkyl is unsubstituted or substituted once, twice or three times by halogen,
—O—(C$_1$–C$_4$)-alkyl, in which alkyl is unsubstituted or substituted once, twice or three times by halogen,
—C(O)—O—R4,
—CN,
—N(R5)-(R6),
—OH,
—S—(C$_1$–C$_4$)-alkyl,
—S(O)—(C$_1$–C$_4$)-alkyl, and
—S(O)$_2$—R7, and R2 is selected from the group consisting of
hydrogen,
halogen,
—C$_1$–C$_4$)-alkyl,
—O—(C$_1$–C4)-alkyl,
—C(O)O—R4,
—CN,
—N(R5)-(R6),
—OH,
—S—(C$_1$–C$_4$)-alkyl,
—S(O)—(C$_1$–C$_4$)-alkyl, and
—S(O)$_2$—R7; or R1 and R2, taken together with the two carbon atoms of ring1 to which R1 and R2 are attached, form a 5- or 6-membered ring which is aromatic or saturated and contains zero, one or two heteroatoms which are independently selected from the group consisting of oxygen, nitrogen and sulfur while R3 is as defined above; or R2 and R3, taken together with the two carbon atoms of ring1 to which R2 and R3 are attached, form a 5- or 6-membered ring which is aromatic or saturated and contains zero, one or two heteroatoms which are independently selected from the group consisting of oxygen, nitrogen and sulfur while R1 is not part of a ring and is as defined above;

R1' and R3' are independently selected from the group consisting of
hydrogen,
halogen,
—(C$_1$–C$_4$)-alkyl, in which alkyl is unsubstituted or substituted once, twice or three tires by halogen,
—O—(C$_1$–C$_4$)-alkyl, in which alkyl is unsubstituted or substituted once, twice or three times by halogen,
—C(O)—O—R4,
—CN,
—N(R5)-(R6),
—OH,
(C$_1$–C$_4$)-alkyl,
—S(O)—-(—C$_1$–C$_4$)-alkyl, and
—S(O)$_2$—R7, and R2' is selected from the group consisting of
hydrogen,
halogen,
—(C$_1$–C$_4$)-alkyl,
—O—(C$_1$–C$_4$)-alkyl,
—C(O)—O—R4,
—CN,
—N(R5)-(R6),
—OH,
—S—(C$_1$–C$_4$)-alkyl,
—S(O)—(C$_1$–C$_4$)-alkyl, and
—S(O)$_2$—R7; or R1' and R2', taken together with the two carbon atoms of ring2 to which R1' and R2' are attached, form a 5- or 6-membered ring which is aromatic or saturated and contains zero, one or two heteroatoms which are independently oxygen, nitrogen and sulfur while R3' is as defined above; or R2' and R3', taken together with the two carbon atoms ring2 to which R2' and R3' are attached, form a 5- or 6-membered ring which is aromatic or saturated and contains zero, one or two heteroatoms which are independently selected from the group consisting of oxygen, nitrogen and sulfur while R1' is not a number of a ring and is as defined above;

R4 is hydrogen or —($C_1$–$C_4$)-alkyl;

R5 and R6 are independently selected from the group consisting of
hydrogen,
—$C_1$–$C_4$)-alkyl,
—C(O)—($C_1$–$C_4$)-alkyl, and
—$O_2$—($C_1$–$C_4$)-alkyl, and R7 is selected from the group consisting of
—($C_1$–$C_4$)-alkyl,
—OH, and
—$NH_2$ and, a stereoisomeric form of the compound of formula I, a mixture of two or more stereoisomeric forms of the compound of formula r, or a physiologically tolerated salt of the compound of formula I, provided that at least one of the radicals R1, R2, R3, R1', R2', R3' is not selected from the group consisting of hydrogen, halogen, nitro, —($C_1$–$C_4$)-alkyl and —O—($C_1$–$C_4$)-alkyl.

10. A method for therapy of a degenerative joint disease comprising administering a compound of formula I as defined in claim 1.

11. A method according to claim 10, wherein R1, R3, R1', R3' are not selected from the group consisting of halogen, unsubstituted —(C1–C4)-alkyl and unsubstituted —O(C1–C4)-alkyl except when there is a 5- or 6-membered ring formed between R1 and R2, or between R2 and R3, or between R1'and R2', or between R2' and R3'.

12. A method according to claim 10, wherein R1, R3, R1', and R3' are independently selected from the group consisting of hydrogen, chlorine, fluorine, trifluoromethyl, methoxy, methyl, —C(O)—OH, —C(O)—O—$CH_3$, —CN, —$NH_2$, —NH—C(O)—$CH_3$, —NH—$SO_2$—$CH_3$, —N—($CH_3$)$_2$, —$SO_2NH_2$, —OH, —O—$CH_2$($CHF_2$), —S—$CH_3$, —S(O)—$CH_3$, —S(O)$_2$—$CH_3$, and bromine; and R2 and R2'are independently selected from the group consisting of hydrogen, chlorine, fluorine, methoxy, methyl, bromine, —C(O)—OH, —C(O)O—$CH_3$, —CN, —$NH_2$, —NH—C(O)—$CH_3$, —NH-$SO_2$—$CH_3$, —N—($CH_3$)$_2$, $SO_2$, —OH, —O—$CH_2$—($CHF_2$), —S—$CH_3$, —S(O)—$CH_3$ and —S(O)$_2$-$CH_3$; or R1 and R2, R2 and R3, R1'and R2', or R2'and R3', together with the two carbon atoms of ring1 or ring2 to which R1 and n, R2 and R3, R1' and R2', or R2' and R3', respectively, are attached, form a dioxolane, dihydrofuran or furan ring, and any R1, R2, R3, R1', R2', or R3' that is not a member of said dioxolane, dihydrofuran or furan ing is as previously defined.

13. A method according to claim 10, wherein R1, R3, R1', and R3'are independently selected from the group consisting of hydrogen, —($C_1$–$C_4$)alkyl, in which alkyl is substituted once, twice or three times by halogen, and —O—($C_1$–$C_4$)-alkyl, in which alkyl is substituted once, twice or tree times by halogen, and R2 and R2' are independently selected from the group consisting of hydrogen, halogen, —O—($C_1$–$C_4$)-alkyl, and —($C_1$–$C_4$)-alkyl; or R1 and R2, R2 and R3, R1'and R2', or R2'and R3', together with the two carbon atoms of ring1 or ring2 to which R1 and R2, R2 and R3, R1' and 2', or R2'and R3', respectively, are attached, form a 5- or 6-membered ring which is aromatic or saturated and contains zero, one or two heteroatoms which are independently selected from the group consisting of oxygen, nitrogen and sulfur, and any R1, R2, 3, R1', R2', or R3' that is not a member of said a 5- or 6-membered ring is independently selected from the group consisting of hydrogen, halogen, —($C_1$–$C_4$)-alkyl, in which alkyl is unsubstituted or substituted once, twice or three times by halogen, and —O—($C_1$–$C_4$)-alkyl, in which alkyl is unsubstituted or substituted once, twice or three times by halogen.

14. A method according to claim 10, wherein R1, R3, R1', and R3'are independently selected from the group consisting of hydrogen and trifluoromethyl, and R2 and R2' are independently selected from the group consisting of hydrogen, chlorine, fluorine, methoxy and methyl; or R1 and R2, R2 and R3, R1'and R2', or R2' and R3', together with the two carbon atoms of ring1 or ring2 to which R1 and R2, R2 and R3, R1'and R2', or R2'and R3', respectively, are attached, form a dioxolane, dihydrofuran or furan ring, and any R1, R2, R3, R1', R2', or R3' that is not a member of said dioxolane, dihydrofuran or furan ring is independently selected from the group consisting of hydrogen, chlorine, fluorine, trifluoromethyl, methoxy, and methyl.

15. A method according to claim 9, wherein said disease is a disease of connective tissue.

16. A method according to claim 15, wherein said disease of connective tissue is collagenoses, periodontal diseases or wound healing disturbances.

17. A method of treatment for breast cancer comprising administering to a patient a compound of formula I as defined in claim 1.

* * * * *